United States Patent [19]

Kojima et al.

[11] Patent Number: 5,041,727
[45] Date of Patent: Aug. 20, 1991

[54] SPECTROPHOTOMETER WITH NEAR INFRARED RADIATION SENSOR HAVING AN IMPROVED SENSITIVITY

[75] Inventors: Masaya Kojima, Katsuta; Sadao Minakawa, Mito, both of Japan

[73] Assignee: Hitachi, Ltd., Tokyo, Japan

[21] Appl. No.: 480,614

[22] Filed: Feb. 15, 1990

[30] Foreign Application Priority Data

Feb. 22, 1989 [JP] Japan .................................. 1-040253

[51] Int. Cl.⁵ .............................................. G01J 5/20
[52] U.S. Cl. ................................. 250/352; 250/370.15
[58] Field of Search ................ 250/370.18, 352, 343, 250/339; 356/323, 325, 51, 319, 332

[56] References Cited

U.S. PATENT DOCUMENTS

| | | | |
|---|---|---|---|
| 3,942,010 | 3/1976 | Peterson et al. | 250/352 |
| 4,323,309 | 4/1982 | Akitomo et al. | 356/319 |
| 4,325,634 | 4/1982 | Tohyama | 356/332 |
| 4,542,295 | 9/1985 | Mattson et al. | 250/352 |
| 4,602,158 | 7/1986 | Barrett . | |
| 4,678,914 | 7/1987 | Melrose et al. . | |
| 4,682,032 | 7/1987 | Barrett | 250/352 |
| 4,734,584 | 3/1988 | Rosenthal . | |
| 4,853,538 | 8/1989 | Jackson | 250/336.2 |

FOREIGN PATENT DOCUMENTS

| | | |
|---|---|---|
| 3007793 | 9/1980 | Fed. Rep. of Germany . |
| 59-203927 | 11/1984 | Japan ................................. 356/319 |

OTHER PUBLICATIONS

Degen et al., "A Method of Trapping GC Fractions for Vibrational Spectroscopic Identification", *Laboratory Practice*, vol. 25, No. 11, pp. 767-768 (Nov. 1976), Publisher: United Trade Press Ltd.

Primary Examiner—Constantine Hannaher
Assistant Examiner—Edward J. Glick
Attorney, Agent, or Firm—Fay, Sharpe, Beall, Fagan, Minnich & McKee

[57] ABSTRACT

The invention relates to a spectrophotometer having a light source capable of alternatively producing near infrared radiation and another radiation other than the near infrared radiation, a dispersing section for dispersing radiation from the light source to provide substantially monochromatic radiation so that a sample is irradiated with the substantially monochromatic radiation to thereby provide sample radiation, and a sensing section for sensing the sample radiation. The sample radiation is subjected to energy absorption of a specific wavelength by the sample. The sensing section includes a first sensing unit having a near infrared radiation sensor, a second sensing unit having a visible/ultraviolet radiation sensor and a temperature control unit for holding the near infrared radiation sensor at a substantially constant temperature lower than the room temperature.

18 Claims, 6 Drawing Sheets

F I G. 10
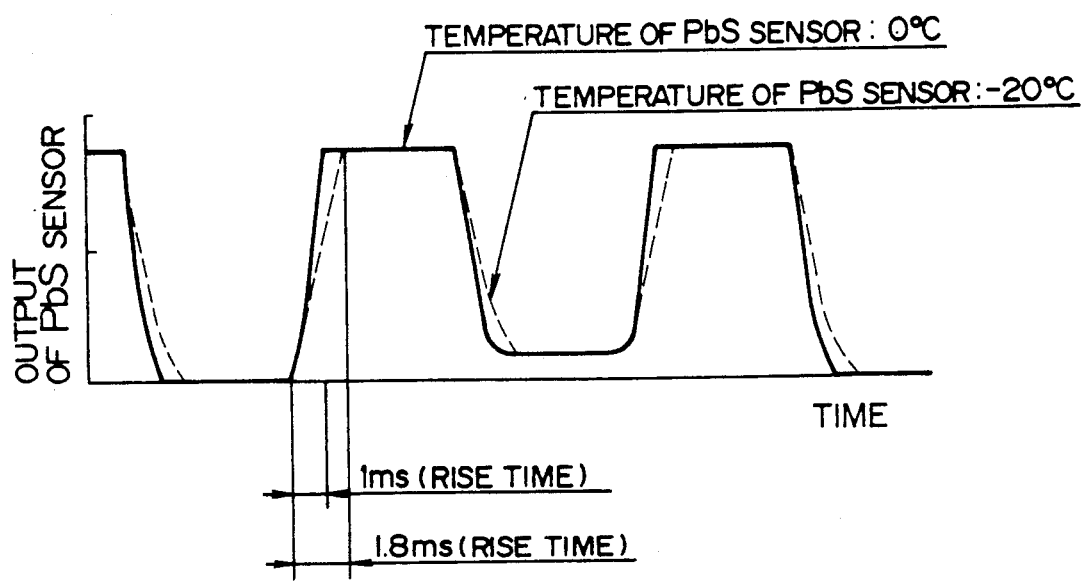

SPECTROPHOTOMETER WITH NEAR INFRARED RADIATION SENSOR HAVING AN IMPROVED SENSITIVITY

BACKGROUND OF THE INVENTION

The present invention relates to a spectrophotometer suitable especially for measurement in a near infrared wavelength region.

In the conventional spectrophotometer, a lead sulfide (PbS) sensor is used as a sensor for the near infrared region under the room temperature.

In the above-mentioned conventional spectrophotometer, the sensitivity of the sensor is low and the S/N (signal-to-noise) ratio thereof is also low in the near infrared region. Further, there is a problem that the sensitivity and response speed of the sensor element for the near infrared region is deteriorated under use at the room temperature.

SUMMARY OF THE INVENTION

It is an object of the present invention to provide a photometer having an improved sensitivity in the measurement in the near infrared wavelength region.

Another object of the present invention is to provide a spectrophotometer having an improved sensitivity in the measurement in the near infrared wavelength region.

Another object of the present invention is to prevent degradation of the sensitivity and/or response speed of a near infrared radiation sensor.

According to one aspect of the present invention, a near infrared radiation sensor is held at a substantially constant temperature lower than the room temperature by temperature control means. The temperature control means may, for example, include a temperature sensing element disposed in the vicinity of the near infrared radiation sensor, a cooling/heating element thermally coupled to the near infrared radiation sensor for cooling/heating it and circuit means responsive to an output of the temperature sensing element for controlling the cooling/heating element to hold the near infrared radiation sensor at the substantially constant temperature lower than the room temperature.

In one embodiment of the present invention, a PbS sensor and a temperature sensing element are disposed on a cooling/heating element to form sensing means.

The temperature detected by the temperature sensing element is compared with a reference temperature so that an electric power (or current) supplied to the electronic cooling/heating element is changed in accordance with a result of the comparison, thereby holding the PbS sensor at a substantially constant temperature lower than the room temperature.

According to one embodiment of the present invention, since a PbS sensor is cooled, it is possible to improve the sensitivity of a spectrophotometer using the PbS detector in a near infrared region and to expand the measurable wavelength range to a longer wavelength side as compared with that at the room temperature. Also, the S/N ratio of an output of the spectrophotometer can be improved by virtue of the improvement in the sensitivity. Further, since the PbS sensor is held at a low and constant temperature, there is an effect that the deterioration of the characteristic (such as the sensitivity and response speed) of the PbS sensor can be prevented.

BRIEF DESCRIPTION OF THE DRAWINGS

FIG. 10 is a characteristic diagram showing output waveforms of the PbS detector, especially, rise times thereof.

DESCRIPTION OF THE PREFERRED EMBODIMENTS

An embodiment of the present invention will now be explained in reference with FIGS. 1 to 5.

Figure 1:
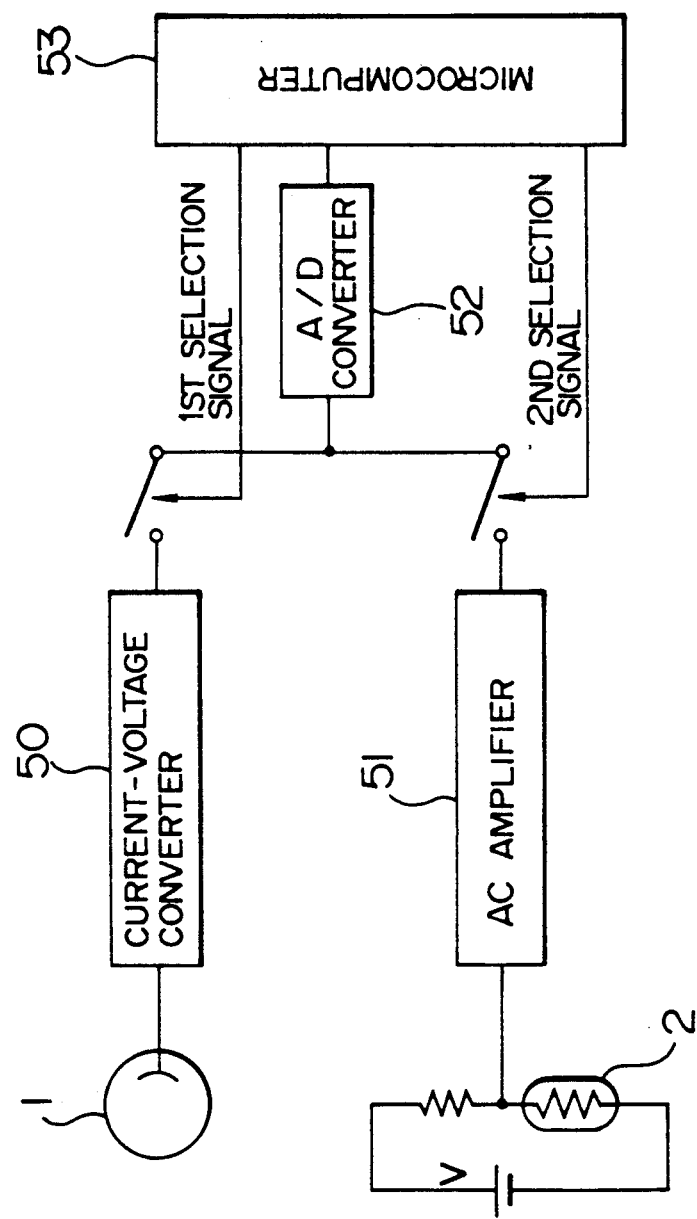
FIG. 1 is a schematic diagram showing changeover of sensors according to an embodiment of the present invention.

FIG. 1 is a schematic diagram showing changeover of sensors, i.e., change-over of the operation wavelength ranges in a spectrophotometer. Light or radiation in an ultraviolet and visible region is detected by a visible/ultraviolet radiation sensing unit constituted by, for example, a photomultiplier 1 an output current of which is converted into a voltage by a current-voltage converter 50. On the other hand, light or radiation in a near infrared region is detected by a near infrared radiation sensing unit constituted by, for example, a PbS sensor 2 an output voltage of which is amplified by an AC amplifier 51. An output signal is always produced from each of the detectors 1 and 2. First and second selection signals generated by a microcomputer 53 effect a change-over between the output signals from the detectors 1 and 2 so as to select either one of the photomultiplier and the PbS sensor in accordance with a wavelength region where measurement is to be made. The output signal of the selected sensor is converted into a digital signal by an A/D converter 52 and is thereafter processed by the microcomputer 53 which in turn provides various results of measurement. Reference symbol V represents an operation power supply for the PbS sensor.

Figure 2:
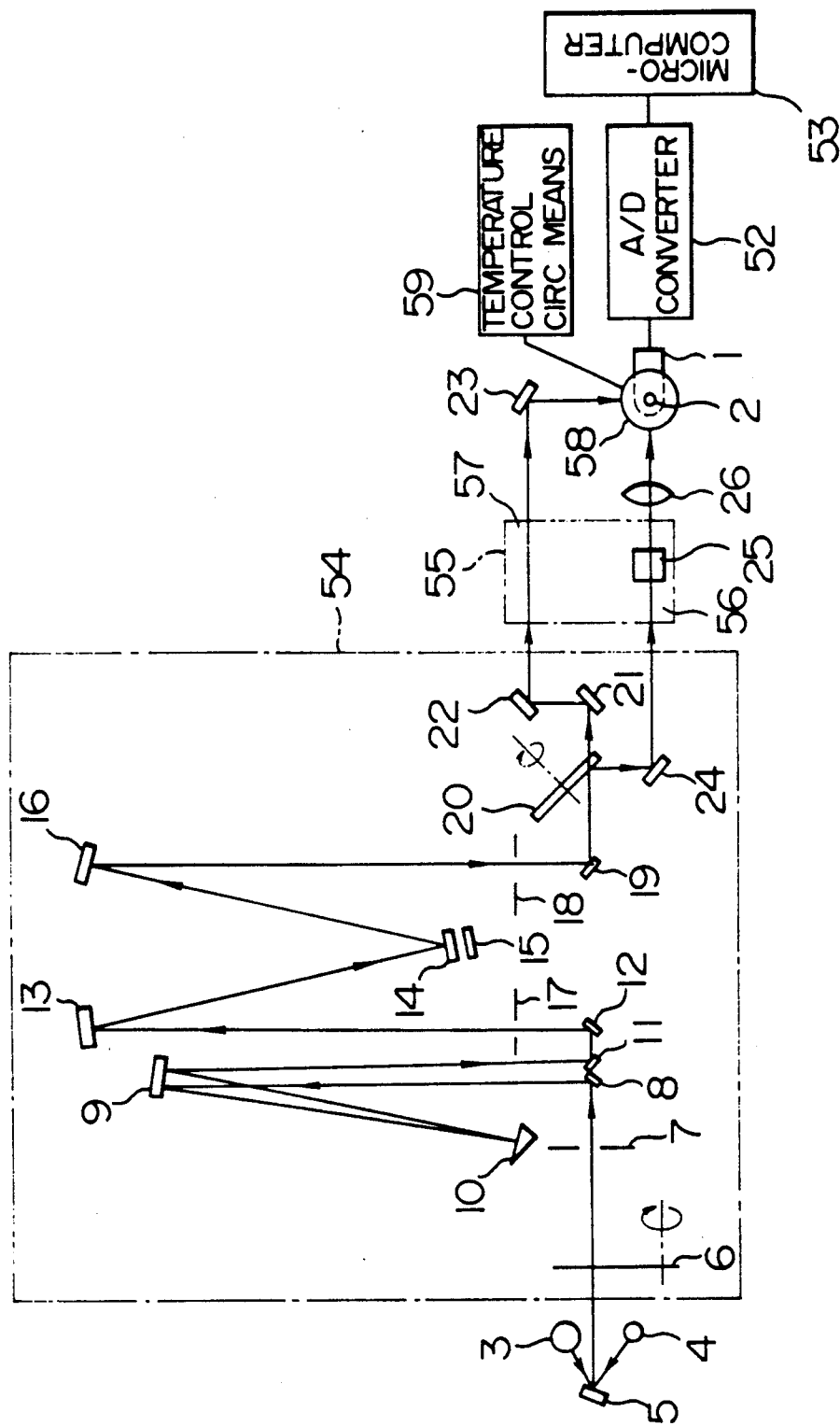
FIG. 2 is a system diagram of the whole of a spectrophotometer according to an embodiment of the present invention.

FIG. 2 shows a system diagram of the whole of a spectrophotometer according to an embodiment of the present invention. Light source means includes a deuterium ($D_2$) lamp 3 constituting a visible/ultraviolet wavelength region light source and a tungsten iodide (WI) lamp 4 constituting a near infrared wavelength region light source, and the lamp 3 or 4 is selected in accordance with wavelengths where measurement is to be made. The lamp selection is effected by changing over the angle of a mirror 5 in accordance with wavelengths. White light (radiation) from the lamp selected corresponding to the wavelength region is conducted into a light dispersing means or a spectroscope device 54. The white light (radiation) introduced into the spectroscope device 54 is chopped by a mechanical chopper 6. The mechanical chopper 6 has a blade or fan which cuts off the white light (radiation) during a quarter period. As the blade of the chopper 6 is rotated, a zero signal representing no passing of light is periodically produced. The light passes through a first slit 7 and are reflected by a toroidal mirror 8 and a concave mirror 9 to enter a prism 10 by which the light (radiation) is dispersed through refraction. The dispersed light (radiation) is reflected by plane mirrors 11 and 12 and is passed through a second slit 17. Further, the light is reflected by a concave mirror 13 and impinges upon a plane diffraction grating 14 for a visible ultraviolet wavelength region or a plane diffraction grating 15 for a near infrared wavelength region by which the light is dispersed. The diffraction gratings 14 and 15 separate the visible ultraviolet radiation and the near infrared radiation from each other and each of the diffraction gratings has a grating constant which is optimum in the corresponding wavelength region. The diffraction gratings 14 and 15 are used with a change-over therebetween in accordance with wavelengths where measurement is to be made.

The light (radiation) dispersed by the diffraction grating 14 or 15 is reflected by a concave mirror 16 to pass a third slit 18 and is reflected by a plane mirror 19 to reach a rotating mirror 20. The light (radiation) reaching the rotating mirror 20 is a highly pure or well defined monochromatic light (radiation) produced by the dispersion at the prims 10 and the diffraction gratings 14 and 15.

The monochromatic light or radiation is separated by the rotating mirror 20 into a sample light (radiation) with which a sample is irradiated and a reference light (radiation). The rotating mirror 20 is divided into four sectors including two opposite or symmetrical sectors on which mirrors (not shown) are provided. As the rotating mirror 20 rotates, there are produced a phase in which the incident light is reflected and a phase in which the incident light is transmitted. The light (radiation) reflected by the rotating mirror 20 is directed to a sample section 56 of a sample chamber 55 by a cylindrical mirror 24 and is passed through a sample 25 or reflected by the sample 25 so that energy of at least one specific component wavelengths of the light (radiation) proper to the sample is absorbed by the sample by the passage through or reflection from the sample 25. The light (radiation) subjected to such absorption passes a lens 26 to enter an integrating sphere 58. On the other hand, the light transmitted through the rotating mirror 20 is directed to a reference section 57 of the sample chamber 55 by a plane mirror 21 and a cylindrical mirror 22 and is reflected by a plane mirror 23 to enter the integrating sphere 58. A photomultiplier 1 is disposed on the rear side of the integrating sphere 58 as seen from the drawing sheet plane and a PbS sensor 2 is disposed in front of the integrating sphere 58 as seen from the drawing sheet plane. Outputs of the photomultiplier 1 and the PbS sensor 2 are supplied through a current-voltage converter (50 as shown in FIG. 1) and an AC amplifier (51 as shown in FIG. 1), respectively, to an A/D converter 52 to which a microcomputer 53 is connected. A temperature control device including circuit means 59 is provided for holding the PbS detector 2 at a substantially constant temperature lower than the room temperature.

Figure 3:
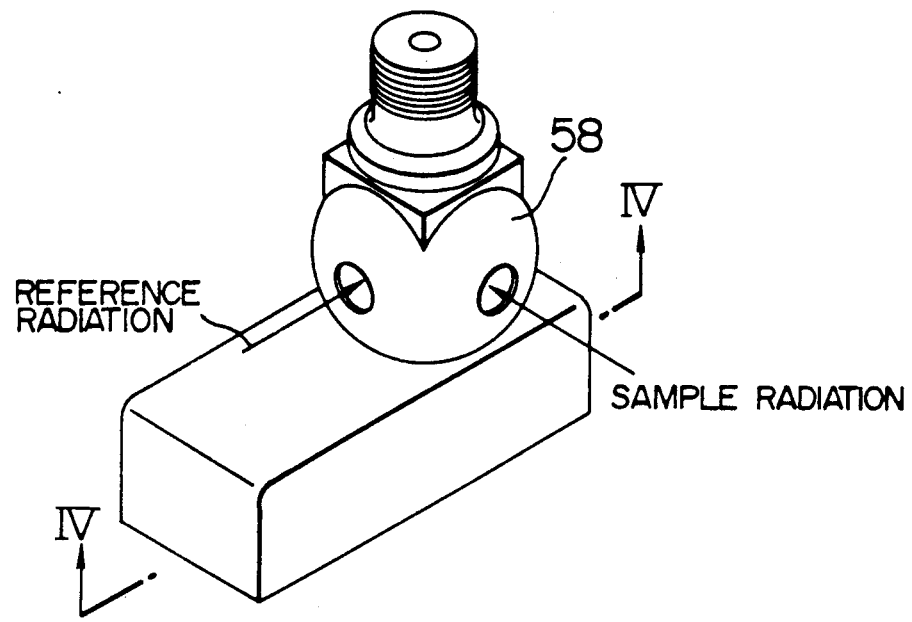
FIG. 3 is a perspective view of a detection section according to an embodiment of the present invention.
Figure 4:
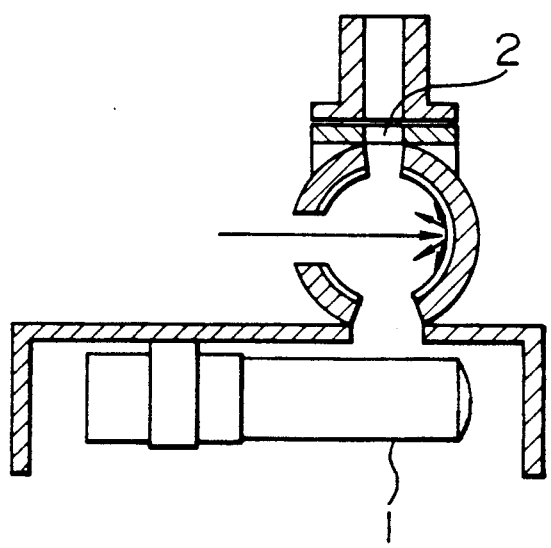
FIG. 4 is a cross section taken along line IV—IV in FIG. 3.

FIG. 3 is a perspective view showing sensing means of a spectrophotometer and FIG. 4 is a cross section taken along line IV—IV in FIG. 3. The sample light (radiation) supplied from the sample and the reference light individually enter the integrating sphere 58 from separate entrance windows thereof and reach the inner surface of the integrating sphere 58. The inner surface of the integrating sphere 58 is coated with barium sulfate and all light rays or the whole radiation reaching the inner surface are uniformly scattered. The scattered light is detected by the photomultiplier 1 constituting a second sensing unit for detection of ultraviolet and visible light disposed on the lower side of an incidence plane of the sample light or otherwise the reference light and by the PbS sensor 2 constituting a first sensing unit for detection of near infrared light disposed on the upper side of the incidence plane, as viewed on the drawing.

Figure 5:
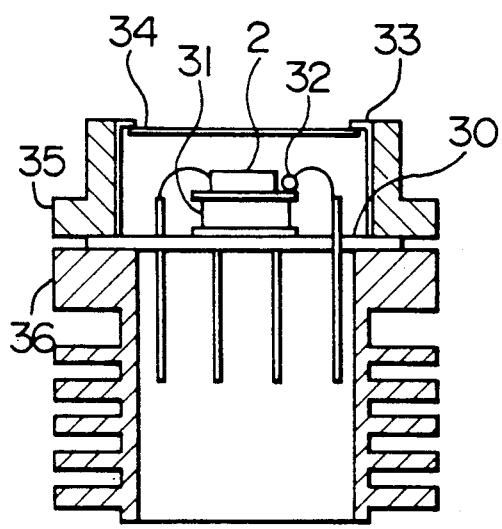
FIG. 5 is a longitudinal cross section of a PbS sensor unit according to the present invention.
Figure 6:
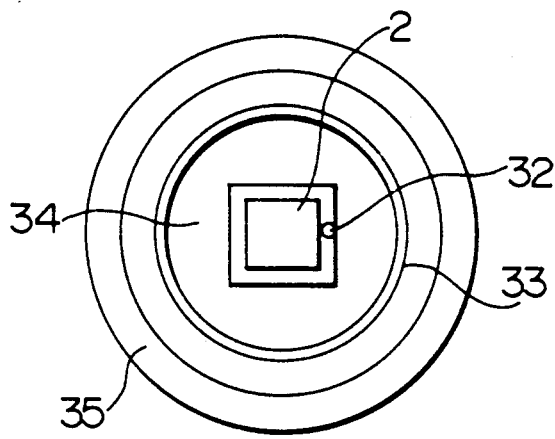
FIG. 6 is a plan view of the PbS sensor unit shown in FIG. 6.

FIGS. 5 and 6 are longitudinal cross sectional and plan views of a first sensing unit having a PbS sensor for detection of near infrared light. Referring to the figures, the PbS sensor 2 is disposed on a surface of a known cooling/heating element, for example, an electronic cooling/heating element 31. A temperature sensing element 32 is disposed in the vicinity of the element 31, for example, is disposed on the same surface as the PbS sensor 2. The electronic cooling/heating element 31 has cooling/heating element pieces disposed on a metal plate 30 having a good thermal conductivity and the whole of the electronic heating/cooling element 31 is isolated from the open or outside air by a metal sleeve 33 and a window 34 made of sapphire. The outer periphery of the structure is provided with radiating fins 35 and 36.

The electronic cooling/heating element 31 can be used for either heating or cooling, depending upon the direction of a current which flows through the element 31.

Figure 7:
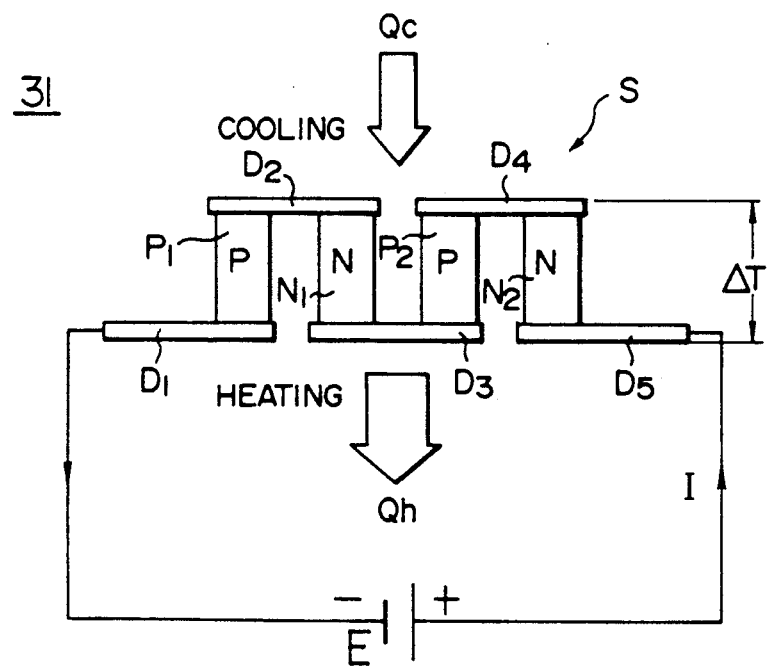
FIG. 7 is a schematic diagram of an electronic cooling/heating device which may be used in an embodiment of the present invention.

FIG. 7 shows an example of an electronic cooling/heating element 31 of a simple structure. The element includes, in principle, a semiconductor assembly S having N-type semiconductor pieces $N_1$, $N_2$, ... and P-type semiconductor pieces $P_1$, $P_2$, ... alternately connected in series with metal pieces $D_1$, $D_2$, ..., and a power source E for supplying DC current to the semiconductor assembly S. When a current I flows in a direction from an N-type semiconductor piece $N_2$ to a P-type semiconductor piece $P_1$, the metal plates $D_2$ and $D_4$ are cooled and take heat ($Q_c$) from surroundings. This is because electrons moving from the P-type semiconductor pieces $P_1$, $P_2$ having a lower energy level to the N-type semiconductor pieces $N_1$, $N_2$ having a higher energy level via metal pieces $D_2$, $D_4$ need energy, which is supplied in the form of heat from the surroundings. The electrons having gained such thermal energy radiate heat $Q_h$ when moving from an N-type semiconductor piece $N_1$ to a P-type semiconductor piece $P_2$ via the metal piece $D_3$. By efficiently dissipating heat $Q_h$ on the higher temperature side, it is possible to move heat from the lower temperature side of the assembly S where metal pieces $D_2$ and $D_4$ exist to the higher temperature side of the assembly S where metal pieces $D_1$, $D_3$ and $D_5$ exist with a temperature difference $\Delta T$ therebetween. Apparently, the higher and lower temperature sides are reversed if the direction of flow of current is reversed.

Turning now back to FIGS. 5 and 6, it is now assumed that current is caused to flow through the electronic cooling/heating element 31 so that the PbS sensor 2 is cooled. As the PbS sensor 2 is cooled, the temperature of the PbS sensor 2 is detected by the temperature sensing element 32 so that a current to be caused to flow through the electronic cooling/heating element 31 is changed, thereby holding the PbS sensor 2 at a substantially constant temperature lower than the room temperature. On the other hand, the heat generated on the opposite side to a cooling surface of the electronic cooling/heating element 31 can be effectively dissipated through the metal plate 30 by the radiating fins 35 and 36.

Figure 8:
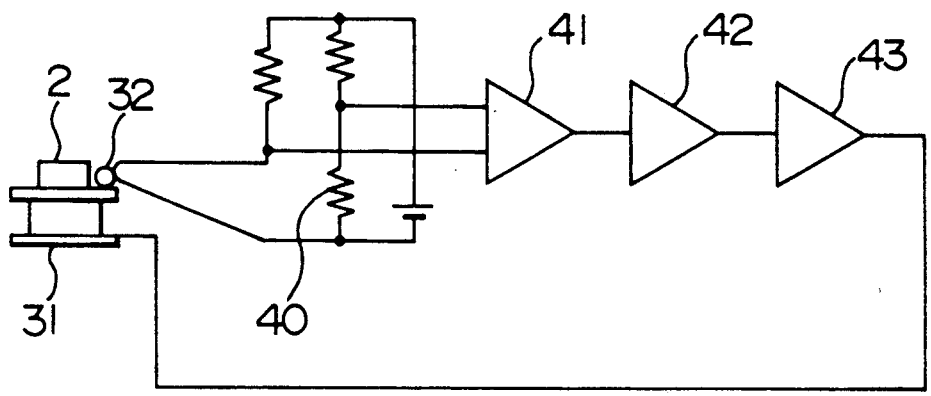
FIG. 8 is a diagram showing a temperature control device for a PbS sensor according to an embodiment of the present invention.

Next, circuit means 59 of the temperature control device for holding the PbS sensor at a substantially constant temperature lower than the room temperature will now be explained by virtue of FIG. 8. The temperature sensing element 32 disposed in the vicinity of the sensor 2 forms a bridge circuit together with a reference resistor 40 corresponding to a set or desired temperature and a measured temperature and the reference or set temperature are compared by a comparator 41. An output of the comparator 41 is amplified by an amplifier 42 and is further current-amplified by a booster device or amplifier 43 which supplies a current to the electronic cooling/heating element 31 thermally coupled to the sensor 2. This temperature control is started simultaneously with power supply to the system so that the PbS sensor 2 is always kept at a constant temperature condition.

Next, examples of measurement obtained by the spectrophotometer according to an embodiment of the present invention will be shown.

Figure 9:
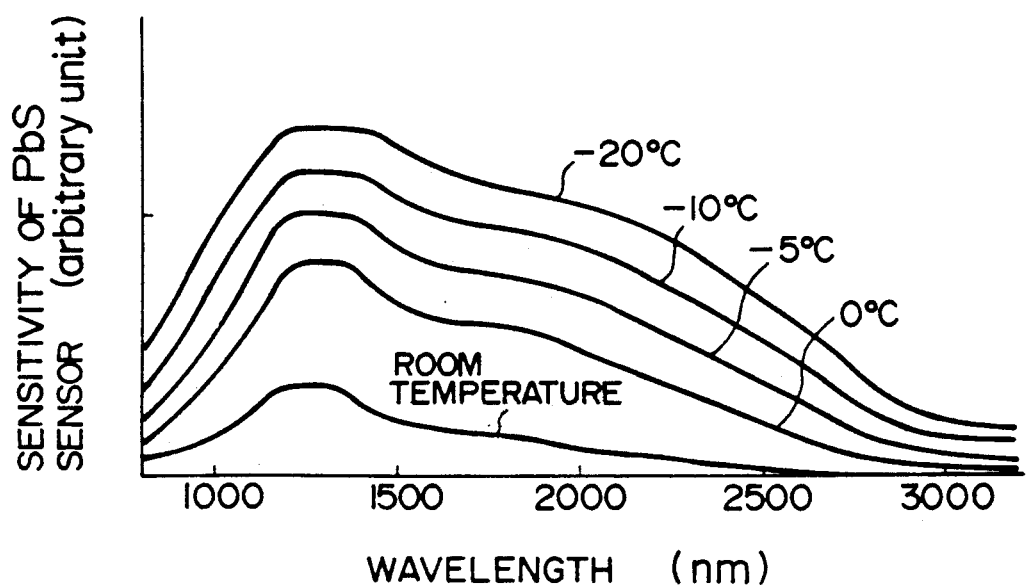
FIG. 9 is a characteristic diagram showing a dependency of measurement wavelengths versus sensor sensitivity upon the temperature when a PbS sensor is cooled.

FIG. 9 shows the detection sensitivity of the PbS sensor measured in a wavelength range of 800 to 3200 nm with the PbS sensor cooled. From the figure, it is seen that as the temperature is made lower than the room temperature, the sensitivity is improved, thereby allowing measurement up to a longer wavelength. For example, regarding the sensitivity when compared in a wavelength region of 1200 to 1400 nm where the maximum sensitivity is obtained, the sensitivities at 0° C., −10° C. and −20° C. are respectively about 2.5 times, 3.5 times and 4.0 times as high as that at the room temperature. Also, regarding wavelengths where measurement is possible, though the longest possible wavelength at the room temperature is about 2600 nm, the longest possible wavelength at the temperatures not higher than 0° C. is expanded up to about 3200 nm with which the measurement of sensitivity was made.

Also, it has been confirmed that the S/N ratio is improved at a factor conformable to the improvement in the sensitivity.

Further, since the PbS sensor can be kept at a low and constant temperature, there is an effect that it is possible to prevent the deterioration of the characteristic (sensitivity and response speed) of the PbS sensor.

FIG. 10 shows rise times of output waveforms of the PbS sensor in the case where the temperature of the sensor is 0° C. and −20° C., respectively. Though the rise time is 1 ms when the temperature of the detector is 0° C., the rise time at −20° C. is 1.8 ms. Namely, the rise time at −20° C. becomes longer than that at 0° C. (by about 56%).

In the case where the temperature of the sensor is set to be lower than substantially −20° C., a relatively long time was required until the temperature is lowered, since the capacity of the electronic cooling/heating element used in the present embodiment is small. Also, it has been found out that a heavy frost adheres to the sensor and the accuracy of measurement may be degraded.

Further, there may arise a problem that the temperature control becomes difficult when the temperature of the sensor is near to the room temperature.

As apparent from the foregoing, when the detection sensitivity, measurable wavelength range, rise time, temperature control, accuracy of measurement, and so on are taken into consideration, it is preferable that the optimum temperature range for the PbS detector according to the present embodiment is substantially 0 to −20° C.

We claim:

1. A near infrared photometer for use in an environment having an environment temperature, comprising:
   a sensing unit having a closed housing and a near infrared radiation sensor disposed in said closed housing; and
   means for holding said near infrared radiation sensor at a substantially constant temperature lower than the environment temperature,
   wherein said holding means includes
   said closed housing provided with heat radiation fins and a window member of a transparent material through which radiation is allowed to enter said sensor, said sensor being spaced from said window member in said closed housing,
   a temperature sensing element disposed in the vicinity of said near infrared radiation sensor in said closed housing, and
   a cooling/heating element disposed in said closed housing and having a cold side section and a hot side section, said near infrared radiation sensor being thermally conductively coupled to said cold side section, while said radiation fins and said window member are thermally conductively coupled to said hot side section.

2. A near infrared photometer according to claim 1, in which said holding means further includes circuit means responsive to an output of said temperature sensing element for controlling said cooling/heating element to hold said sensor at said substantially constant temperature.

3. A spectrophotometer comprising:
   light source means capable of alternatively producing near infrared radiation and visible/ultraviolet radiation;
   means for dispersing radiation from said light source means to provide substantially monochromatic radiation, said substantially monochromatic radiation from said dispersing means being directed to a sample for irradiation of the sample, with said substantially monochromatic radiation being subjected to energy absorption by the sample to thereby provide a sample radiation, said energy absorption being effected with respect to at least one specific wavelength proper to the sample; and
   means for sensing said sample radiation, said sensing means including a first sensing unit having a near infrared radiation sensor, a second sensing unit having a visible/ultraviolet radiation sensor and means for holding said near infrared radiation sensor at a substantially constant temperature lower than the room temperature,
   wherein said holding means includes a closed housing provided with heat radiation fins and a window member of a transparent material through which radiation is allowed to enter said near infrared radiation sensor, said near infrared radiation sensor being spaced from said window member in said closed housing, a temperature sensing element disposed in the vicinity of said near infrared radiation sensor in said closed housing, and a cooling/heating element disposed in said closed housing and having a cold side section and a hot side section, said near infrared radiation sensor being thermally conductively coupled to said cold side section, while said radiation fins and said window member are thermally conductively coupled to said hot side section.

4. A spectrophotometer according to claim 3, in which said holding means further includes circuit means responsive to an output of said temperature sensing element for controlling said cooling/heating element to hold said near infrared radiation sensor at said substantially constant temperature.

5. A spectrophotometer according to claim 1, wherein said infrared radiation sensor includes a PbS sensor.

6. A spectrophotometer according to claim 3, wherein said infrared radiation sensor includes a PbS sensor.

7. A spectrophotometer according to claim 1, wherein said substantially constant temperature is in a range from 0° C. to −20° C.

8. A spectrophotometer according to claim 3, wherein said substantially constant temperature is in a range from 0° C. to −20° C.

9. A spectrophotometer according to claim 5, wherein said PbS sensor is on a surface and said temperature sensing element is on the same surface as said PbS sensor.

10. A spectrophotometer according to claim 6, wherein said PbS sensor is on a surface and said temperature sensing element on the same surface as said PbS sensor.

11. A spectrophotometer according to claim 5, wherein said substantially constant temperature is in a range from 0° C. to −20° C.

12. A spectrophotometer according to claim 6, wherein said substantially constant temperature is in a range from 0° C. to −20° C.

13. A spectrophotometer according to claim 2, wherein said near infrared radiation sensor includes a PbS sensor.

14. A spectrophotometer according to claim 4, wherein said near infrared radiation sensor includes a PbS sensor.

15. A spectrophotometer according to claim 13, wherein said PbS sensor is on a surface and said temperature sensing element is on the same surface as said PbS sensor.

16. A spectrophotometer according to claim 14, wherein said PbS sensor is on a surface and said temperature sensing element is on the same surface as said PbS sensor.

17. A spectrophotometer according to claim 15, wherein said substantially constant temperature is in a range from 0° C. to −20° C.

18. A spectrophotometer according to claim 16, wherein said substantially constant temperature is in a range from 0° C. to −20° C.

* * * * *